United States Patent [19]

Simonutti et al.

[11] Patent Number: 4,955,387
[45] Date of Patent: Sep. 11, 1990

[54] METHOD AND APPARATUS FOR GUILT DETECTION

[76] Inventors: Paolo Simonutti, 1 Tony St., Harmelia, 1406; John O. Speedy, 11 Rietbok Rd., Robinhills, Randburg, both of Transvsal, South Africa

[21] Appl. No.: 738,215
[22] Filed: May 28, 1985

[30] Foreign Application Priority Data

May 28, 1984 [ZA] South Africa ............... 84/4033

[51] Int. Cl.$^5$ ............................................. A61B 5/024
[52] U.S. Cl. ..................................... 128/687; 340/574
[58] Field of Search ............................... 128/687–690, 128/670–671; 340/573–574

[56] References Cited

U.S. PATENT DOCUMENTS

| 3,661,147 | 5/1972 | Mason et al. ............... 128/689 |
| 3,717,140 | 2/1973 | Greenwood ................. 128/689 |
| 4,060,039 | 11/1977 | Lagarigue ............... 340/574 X |
| 4,085,740 | 4/1978 | Allen, Jr. ................. 128/687 X |
| 4,086,916 | 5/1978 | Freeman et al. ........... 128/690 X |
| 4,100,536 | 7/1978 | Ball et al. ................. 128/689 X |
| 4,120,296 | 10/1978 | Prinz ........................ 128/690 |

FOREIGN PATENT DOCUMENTS

| 2922542 | 12/1879 | Fed. Rep. of Germany ...... 128/689 |
| 2915912 | 10/1980 | Fed. Rep. of Germany ...... 128/689 |
| 2073436 | 10/1981 | United Kingdom ............... 340/573 |

Primary Examiner—Angela D. Sykes
Attorney, Agent, or Firm—Panitch Schwarze Jacobs & Nadel

[57] ABSTRACT

An abnormally high pulse rate is an indicator of personal stress and can therefore be used to test persons for a guilty frame of mind which may, for instance be caused by an attempted theft by an employee from the premises where he works. An instantaneously measured pulse rate is compared with an average pulse rate computed from a past history of pulse rate measurements conducted in respect of the particular person under test. A discernable signal is produced if the instantaneous pulse rate exceeds the average by more than a predetermined amount. In cases where there is no average pulse rate, for instance where the person under test is a first time visitor to the premises, the instantaneous pulse rate is compared with a predetermined pulse rate.

13 Claims, 1 Drawing Sheet

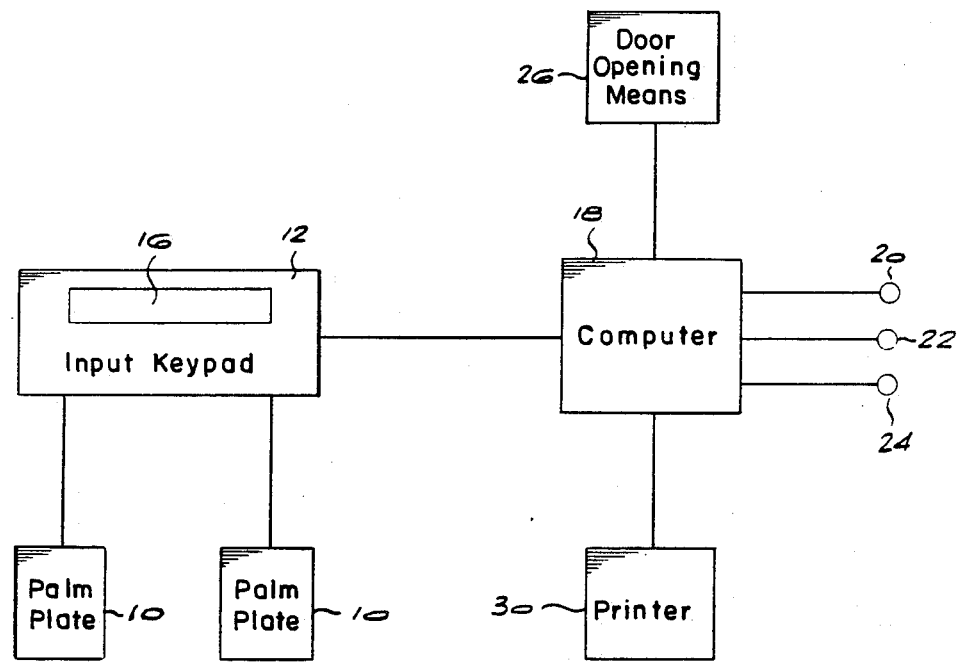

METHOD AND APPARATUS FOR GUILT DETECTION

BACKGROUND TO THE INVENTION

This invention relates to the detection of a guilty state of mind.

Theft of goods by employees is a problem faced by a number of employers. It is therefore common for employers to be searched or interrogated as they leave their work premises each evening. Where there are many employees, it is impractical to subject all of them to search or interrogation, and usually only randomly selected employees are so subjected. Despite the deterrent of a possible search, thefts continue.

It is known that a guilty state of mind will generally increase the level of personal stress and that a high level of stress can be evidenced by, inter alia, an elevated pulse rate.

The present invention seeks to provide a method and means whereby this phenomenon can be used to detect persons who have a guilty state of mind.

SUMMARY OF THE INVENTION

According to one aspect of the invention, there is provided a method of detecting which persons in a group of persons have a guilty state of mind, the method including testing the persons one by one to measure their instantaneous pulse rates, comparing the instantaneously measured pulse rates with average pulse rates computed from histories of pulse rate measurements conducted in respect of the same persons and selecting for search or interrogation those persons whose instantaneous pulse rate is greater than their average pulse rate by more than a predetermined amount.

According to another aspect of the invention, there is provided a method of combatting theft from a premises, the method including the steps of individually subjecting persons leaving the premises to tests in which their instantaneous pulse rates are measured, comparing the instantaneously measured pulse rates with stored average pulse rates computed from histories of pulse rate measurements conducted in respect of the same persons, or, if there is no stored average pulse rate, with a preselected pulse rate, and selecting for search or interrogation those persons whose instantaneously measured pulse rate exceeds their average pulse rate or the preselected pulse rate, as the case may be, by more than a predetermined amount.

The invention also provides apparatus for use in combatting theft from a premises, the apparatus including a pulse rate detector which comprises detector plates to be contacted by the palms of persons leaving the premises and means responsive to the pulses detected by the plates to compute an instantaneous pulse rate reading, means for comparing the instantaneous pulse rate with a stored average pulse rate computed from a history of pulse rate measurements conducted in respect of that person or, in cases where there is no stored average pulse rate, with a preselected pulse rate, and means for producing a discernable signal at least when the instantaneous pulse rate exceeds the average pulse rate or preselected pulse rate, as the case may be.

Preferably, a person's instantaneous pulse rate is computed as an average on the basis of a plurality of pulse-to-pulse time lapses, the time lapses used in the computation being those which do not differ from one another by more than a predetermined amount.

BRIEF DESCRIPTION OF THE DRAWING

The sole FIGURE is a schematic representation of apparatus according to the invention.

DESCRIPTION OF AN EMBODIMENT

The illustrated apparatus is intended for installation at an exit checkpoint from working premises to give an indication to an operator manning the apparatus of persons whose pulse rate is abnormal and who may well be guilty of unlawful behaviour, such as theft from the premises.

Referring to the FIGURE, the numerals 10 represent palm plates of conventional type on which each person to be tested places his palms for detection of his pulse. At the same time, the operator keys into an input keypad 12 the person's reference number, such as an employee reference number obtained from his employee reference card. The keypad includes a visual display 16 on which is displayed the number keyed in to enable the operator to check the correctness of his entry.

Once the operator is satisfied that that entry is correct, he manipulates the keypad to feed the number to a computer 18 which includes a RAM data bank. The data bank stores average pulse rates for a great number of persons which have been computed by the computer from previous tests conducted on those persons.

In order to obtain a reliable actual pulse rate measurement, it is not sufficient merely to measure the time lapse between one pulse and the next, since it is a fact that this time lapse does not always remain constant. The computer therefore computes the actual pulse rate as being the average of four such time lapses which differ from one another by an amount not greater than a predetermined amount. In other words, it may be necessary for more than four pulse-to-pulse time lapses to be analysed by the computer in order for it to compute an average of four time lapses which are sufficiently close to one another.

The computer accesses the data bank and compares the past average pulse rate with that actually computed in the present test. If the actual pulse rate exceeds the accessed average by more than 20 beats per minute, (BPM) but less than 45 BPM, the computer generates a signal which energises a visible light 20 to indicate to the operator that an abnormal pulse rate has been detected and that further investigation is advisable. If the comparison reveals a difference of more than 45 BPM, a light 22 is energised to indicate to the operator that an extremely abnormal pulse has been detected, and that a more stringent search or interrogation than would normally be conducted is necessary.

If the comparison indicates a difference of less than 20 BPM, the computer energises another light 24 which indicates to the operator that further investigation is probably not necessary.

If the comparison reveals a difference greater than 20 BPM, the stored average is not updated, while if it is less than 20 BPM, it is. In this way, the average is not influenced by a single abnormal measurement.

The apparatus may also include means 26 which serve automatically to open one of two or three doors leading to an exit, or to one or more search/interrogation rooms through which the person may leave the checkpoint depending on which light has been energised.

The apparatus also enables the operator to over-ride the computer. If, for instance, the operator has reason to suspect any particular person, he pre-programmes the computer to energise the light 20 or 22 as soon as that person's number is keyed in, irrespective of what the computer's comparison may indicate. In this way, persons who could possibly exhibit a pulse rate within normal limits and would complain if they were subjected to further investigation although the lights 24 were showing, would be unaware of the operator's activities.

In making this invention, the inventors considered various ways in which persons could attempt to foil the test. For instance, persons guilty of unlawful behaviour and aware that they will probably be subjected to intensive interrogation or search could take pulse-rate depressing drugs. The computer could easily be programmed to indicate to the operator (and to open one of the search doors) if an abnormally low pulse rate is revealed, i.e. the existence of an abnormally low pulse rate may also result in search or interrogation.

It will happen that a number of persons, such as visitors, about whom no past pulse rate history has been accumulated will also be required to pass through the check-point. In this case, the operator keys into the computer a special visitor's code number and the computer will then compare the actual pulse rate with a standard preselected pulse rate of 80 BPM, which the inventors have found is an average pulse rate for tests conducted on a great number of persons. The indications given to the operator will be the same as described previously if the actual pulse rate differs from the set rate of 80 BPM by less than 20 BPM, more than 20 BPM but less than 45 BPM, or more than 45 BPM.

The apparatus may also include a printer 30 which provides the operator with a hard-copy print-out of the results of each test where abnormal pulse rates have been measured.

We claim:

1. Apparatus for use in combatting theft from a premises, comprising a pulse rate detector having detector plates adapted to be contacted by the palms of a person leaving the premises and means responsive to the pulses detected by the plates to compute an instantaneous pulse rate reading, means for comparing the instantaneous pulse rate with a predetermined pulse rate, means for producing a discernible signal at least when the instantaneous pulse rate exceeds the predetermined pulse rate, said means for comparing including means for comparing the instantaneous pulse rate with a stored average pulse rate computed from a history of pulse rate measurements conducted in respect of that person, and means for updating the stored average pulse rate with the instantaneous pulse rate, but only when the instantaneous pulse rate does not exceed the stored averaged pulse rate by more than a predetermined amount.

2. The apparatus of claim 1, in which the signal producing means produces a first discernible signal whenever the instantaneous pulse rate is between 20 beats per minute and 45 beats per minute greater than the average pulse rate computed from a history of pulse rate measurements conducted on that person.

3. The apparatus of claim 2, in which the signal producing means produces a different discernible signal whenever the instantaneous pulse rate exceeds the average pulse rate by more than 45 beats per minute.

4. The apparatus of claim 1, in which the means for computing the instantaneous pulse rate performs its computation on the basis of a plurality of pulse-to-pulse time lapses, those lapses used in the computation being lapses which do not differ from one another by more than a predetermined amount.

5. The apparatus of claim 1, in which the signal producing means produces a first discernible signal whenever the instantaneous pulse rate is between 100 and 125 beats per minute.

6. The apparatus of claim 5, in which the signal producing means produces a different discernible signal whenever the instantaneous pulse rate exceeds 125 beats per minute.

7. A method of combatting theft from a premises comprising the steps of individually subjecting persons leaving the premises to tests in which their instantaneous pulse rates are measured, comparing the instantaneously measured pulse rates with a predetermined pulse rate, selecting for search or interrogation those persons whose instantaneously measured pulse rate exceeds the predetermined pulse rate, computing a stored average pulse rate for the individual persons subjected to the test from histories of the pulse rate measurements conducted with respect to the same persons, the predetermined pulse rate being the stored average pulse rate, updating the stored average pulse rate by the instantaneously measured pulse rate, but only if the instantaneously measured pulse rate does not differ from the stored average pulse rate more than a predetermined number of beats per minute.

8. The method of claim 7 including selecting for search or interrogation those persons whose instantaneously measured pulse rate exceeds their average pulse rate by more than 20 beats per minute.

9. The method of claim 7 including selecting for search or interrogation those persons whose instantaneously measured pulse rate exceeds their average pulse rate by more than 45 beats per minute.

10. The method of claim 7, including measuring a person's instantaneous pulse rate by analysing a plurality of pulse-to-pulse time lapses in order to compute an average instantaneous pulse rate for that person, the time lapses which are used in the computation being those which do not differ from one another by more than a predetermined amount.

11. The method of claim 7, in which the average pulse rate is updated only if the instantaneously measured pulse rate exceeds the existing average by no more than 20 beats per minute.

12. The method of claim 7 including selecting for search or interrogation those persons whose instantaneously measured pulse rate exceeds 125 beats per minute.

13. The method of claim 7 including measuring a person's instantaneous pulse rate by analysing the plurality of pulse-to-pulse time lapses in order to compute an average instantaneous pulse rate for that person, the time lapses which are used in the computation being those which do not differ from one another by more than a predetermined amount.

* * * * *